US012697486B2

(12) United States Patent
Anikeeva et al.

(10) Patent No.: US 12,697,486 B2
(45) Date of Patent: Aug. 4, 2026

(54) STRETCHABLE MICROELECTRONIC FIBERS AND THEIR ASSEMBLIES AS MULTIFUNCTIONAL BIOELECTRONIC INTERFACES FOR WHOLE ORGANS

(71) Applicant: Massachusetts Institute of Technology, Cambridge, MA (US)

(72) Inventors: Polina Olegovna Anikeeva, Lexington, MA (US); Atharva Sahasrabudhe, Cambridge, MA (US); Rajib Mondal, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 679 days.

(21) Appl. No.: 18/167,128

(22) Filed: Feb. 10, 2023

(65) Prior Publication Data

US 2023/0321431 A1      Oct. 12, 2023

Related U.S. Application Data

(60) Provisional application No. 63/330,068, filed on Apr. 12, 2022.

(51) Int. Cl.
*A61B 5/256* (2021.01)
*A61B 5/00* (2006.01)
(Continued)

(52) U.S. Cl.
CPC .............. *A61N 1/0509* (2013.01); *A61B 5/01* (2013.01); *A61B 5/257* (2021.01); *A61B 5/4238* (2013.01);
(Continued)

(58) Field of Classification Search
CPC .............. A61N 1/00509; A61N 1/0603; A61N 1/0622; A61N 2005/0609; A61L 31/022; A61L 31/06; A61B 2562/0261
See application file for complete search history.

(56) References Cited

U.S. PATENT DOCUMENTS

2013/0041235 A1* 2/2013 Rogers ..................... A61N 1/05
                                                       600/386
2019/0047240 A1* 2/2019 Sorin ....................... H01B 3/30

FOREIGN PATENT DOCUMENTS

CN       114760912 A  *  7/2022  ......... A61N 1/36117

OTHER PUBLICATIONS

Global Market Report on Bioelectronic Medicine 2019-2029 From IDTechEx Research. Dec. 21, 2018; Available at: https://www.prnewswire.com/news-releases/global-market-report-on-bioelectronic-medicine-2019-2029-from-idtechex-research-300769900.html. (Accessed: Sep. 27, 2021), 13 pages.
(Continued)

*Primary Examiner* — Eun Hwa Kim
(74) *Attorney, Agent, or Firm* — Smith Baluch LLP

(57)        ABSTRACT

A soft, stretchable, multifunctional bioelectronic interface can be used to monitor and/or modulate an entire organ, such as a stomach, heart, bladder, or spinal cord. The interface's softness translates to reduced mechanical mismatch with the tissue, and the interface's stretchability reduces interfacial stress with dynamically expanding and contracting organs. The electronics are stretchable thanks in part to liquid-metal conductors sealed within hollow channels of elastomeric fibers embedded in the interface. The liquid metal is largely strain-insensitive, non-toxic, and has a melting point of less than 37° C., so it remains liquid when implanted in a mammalian body. The liquid metal conductors connect microelectronic components, such as micro light-emitting diodes (μLEDs), electrodes, photodiodes, and temperature sensors, to a flexible printed circuit board (fPCB) at one end of the fiber. The interface may include other microelectronic components, such as piezoelectric strain sensors, that are also coupled to the fPCB.

20 Claims, 10 Drawing Sheets

(51) Int. Cl.

| | |
|---|---|
| *A61B 5/01* | (2006.01) |
| *A61B 5/257* | (2021.01) |
| *A61B 5/265* | (2021.01) |
| *A61B 5/268* | (2021.01) |
| *A61L 31/02* | (2006.01) |
| *A61L 31/06* | (2006.01) |
| *A61N 1/05* | (2006.01) |
| *A61N 5/06* | (2006.01) |

(52) U.S. Cl.
CPC ............. *A61L 31/022* (2013.01); *A61L 31/06* (2013.01); *A61N 5/0603* (2013.01); *A61N 5/0622* (2013.01); *A61B 2562/0261* (2013.01); *A61B 2562/125* (2013.01); *A61N 2005/0609* (2013.01)

(56) References Cited

OTHER PUBLICATIONS

Jeong et al. Soft Materials in Neuroengineering for Hard Problems in Neuroscience. Neuron 86.1 (2015): 175-186.

Lacour et al. "Materials and technologies for soft implantable neuroprostheses." Nature Reviews Materials 1.10 (2016): 1-14.

Minev et al. Electronic dura mater for long-term multimodal neural interfaces. Science 347.6218 (2015): 159-163.

Park et al. Soft, stretchable, fully implantable miniaturized optoelectronic systems for wireless optogenetics. Nature Biotechnology 33.12 (2015): 1280-1286.

Tsao, Bioelectronic Medicine 2019-2029: IDTechEx. Available at: https://www.idtechex.com/en/research-report/bioelectronic-medicine-2019-2029/643. (Accessed: Sep. 27, 2021), 5 pages.

* cited by examiner

100

Electrode pads 160

Adhesion layer 150

Functionalization layer 140

Fiber-based strain sensor 130

Low-modulus silicone layers 120

Soft microelectronic fibers 200

Bottom insulation layer 110

112

160    100    200

5mm

100

1cm

200

240 PMMA

220 CSEBS

230 Ga

210 SEBS

240

212a     212c

212b

200

Interconnect resistance of Ga vs Strain

0% strain

20% strain

50% strain

75% strain

100% strain

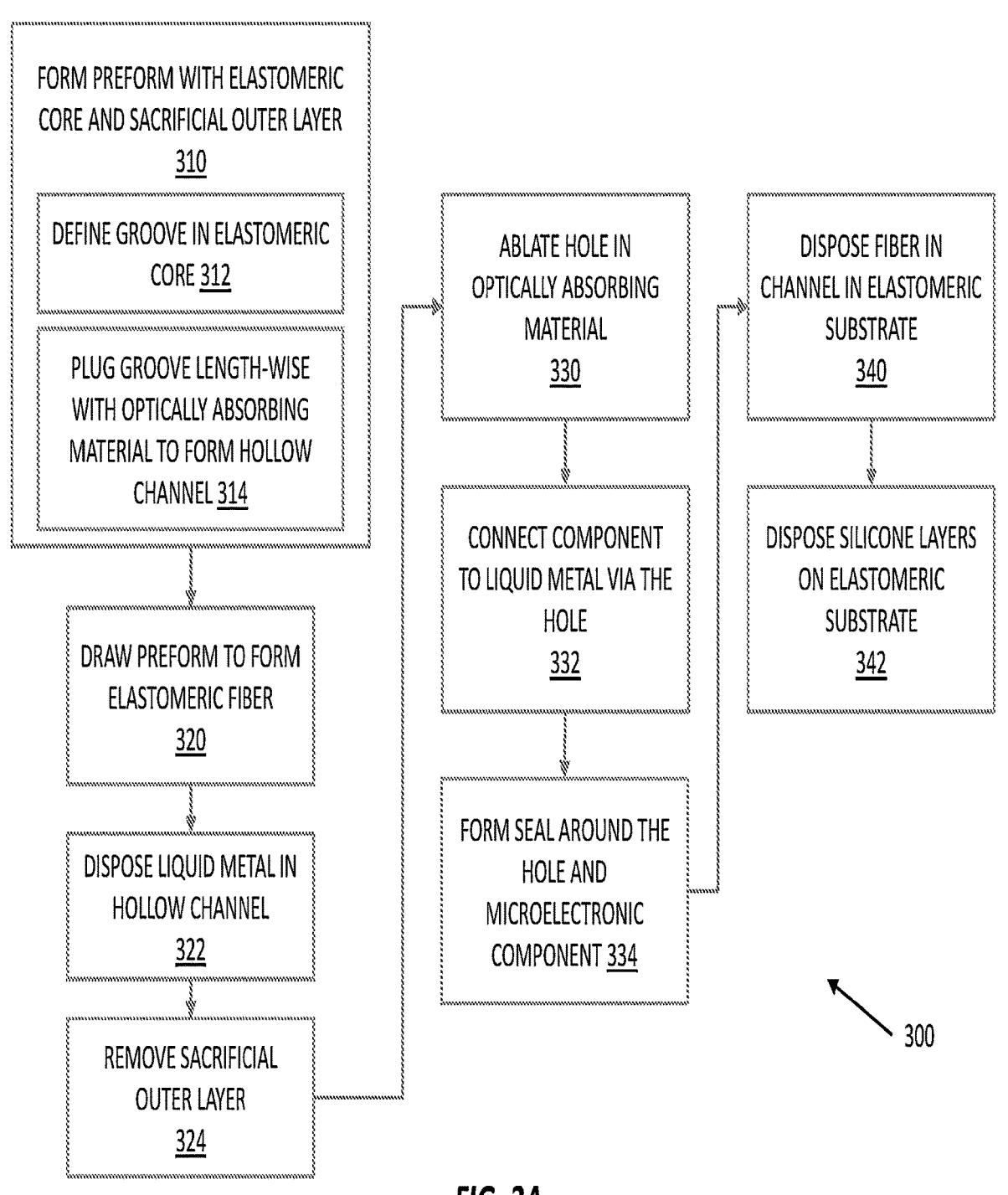

FORM PREFORM WITH ELASTOMERIC CORE AND SACRIFICIAL OUTER LAYER
310

DEFINE GROOVE IN ELASTOMERIC CORE 312

PLUG GROOVE LENGTH-WISE WITH OPTICALLY ABSORBING MATERIAL TO FORM HOLLOW CHANNEL 314

DRAW PREFORM TO FORM ELASTOMERIC FIBER
320

DISPOSE LIQUID METAL IN HOLLOW CHANNEL
322

REMOVE SACRIFICIAL OUTER LAYER
324

ABLATE HOLE IN OPTICALLY ABSORBING MATERIAL
330

CONNECT COMPONENT TO LIQUID METAL VIA THE HOLE
332

FORM SEAL AROUND THE HOLE AND MICROELECTRONIC COMPONENT 334

DISPOSE FIBER IN CHANNEL IN ELASTOMERIC SUBSTRATE
340

DISPOSE SILICONE LAYERS ON ELASTOMERIC SUBSTRATE
342

*Process flow for making soft electrodes for stimulation or recording* x = 0mm　　　x = 40mm

STRETCHABLE MICROELECTRONIC FIBERS AND THEIR ASSEMBLIES AS MULTIFUNCTIONAL BIOELECTRONIC INTERFACES FOR WHOLE ORGANS

CROSS-REFERENCE TO RELATED APPLICATION(S)

This application claims the priority benefit, under 35 U.S.C. 119(e), of U.S. Application No. 63/330,068, filed Apr. 12, 2022, which is incorporated herein by reference in its entirety for all purposes.

GOVERNMENT SUPPORT

This invention was made with government support under NS115025 awarded by the National Institutes of Health. The government has certain rights in the invention.

BACKGROUND

Bioelectronic medicine is an emerging approach to detecting and treating diseases that uses electrical sensing and stimulation of the body's nervous system as an adjunct or alternative to drugs. At the heart of this approach lies a technological component in the form of soft, tissue-compatible medical device that can be chronically interfaced with diverse organ systems while enabling clinical-quality physiological recording and stimulation capabilities. However, fabrication of strain-insensitive and low-modulus elastic conductive networks to power soft circuits in such medical devices has been a long-standing challenge. Large-area scalable fabrication, high electrical conductivity, and robust, reliable mechanical performance are some of the essential, but not co-existent attributes in state-of-the-art approaches.

Previous attempts at developing soft medical interfaces have almost exclusively relied on complex microfabrication approaches that suffer from poor size and number scalability and require access to resource-intensive cleanrooms. In this fabrication route, stretchability is engineered in a high-modulus (e.g., roughly 10 GPa) solid conductor through geometric patterns at the micro- and/or nano-scale. Subsequently, the integration of such fragile metal patterns onto soft elastomeric substrates is achieved through a series of transfer printing steps that scale poorly with the wafer area, often resulting in low device yields. The same geometric designs that enable stretchability in rigid materials also limit their elasticity to pre-defined strains and directions. Related approaches leveraging thin, micro-cracked metal films encapsulated in elastomers offer multiaxial stretchability up to about 5-8%; however, they suffer from poor conductivity, which may be detrimental to designing large area medical devices spanning whole organ surfaces.

SUMMARY

Soft and stretchable bioelectronic interfaces can be made from elastic microelectronic fibers, also called elastomeric fibers, produced through thermal drawing. These fibers can be packaged into a 2D assembly that can be used as a low-modulus, multifunctional laminate for an organ surface (e.g., the serosal surface of the stomach, heart, bladder, skeletal muscle, and spinal cord). The interfaces can be utilized in developing bioelectronic therapies as an implantable neurotechnology. For instance, they can be used to ontogenetically stimulate innervated organs of the central and/or the peripheral nervous system in rodent models of specific disorders while also sensing physiological signals.

An implantable, soft, and stretchable bioelectronic interface for an organ can include an elastomeric (e.g., silicone) substrate having a channel therein, an elastomeric fiber disposed in the channel, liquid metal disposed in a hollow channel defined in or by the elastomeric fiber, and a microelectronic component secured to the elastomeric substrate and in electrical communication with the liquid metal. The microelectronic component can stimulate and/or sense the organ physiology in response to an electrical signal and/or electrical power carried by the liquid metal.

The liquid metal can comprise at least one of Gallium, eutectic Gallium-Indium, or Gallium-Indium-Tin alloy. The liquid metal can be non-toxic and can have a melting point of less than 37° C. The microelectronic component can include a micro light-emitting diode to optically stimulate the organ and/or a temperature sensor to sense a temperature of the organ. Other suitable microelectronic components include but are not limited to photodiodes, pressure sensors, strain sensors, or recording electrodes.

The implantable, soft, and stretchable bioelectronic interface can also include an adhesive layer to adhere the implantable apparatus to a surface of the organ. And it can include a strain sensor, sandwiched between the elastomeric substrate and the adhesive layer, to sense strain experienced by the organ. It can also include a functionalization layer, sandwiched between the elastomeric substrate and the adhesive layer, to increase adhesion of the elastomeric substrate to the adhesive layer.

An implantable, soft, and stretchable bioelectronic interface can be made by forming a preform comprising an elastomeric substrate that defines a channel and a sacrificial outer layer. The elastomeric substrate is drawn to form an elastomeric fiber having the channel oriented along a length of the elastomeric fiber, then the sacrificial outer layer is removed from the elastomeric fiber. Liquid metal is disposed in the channel and electrically connected to a microelectronic component, e.g., by ablating a hole in the elastomeric fiber with a femtosecond/picosecond pulsed laser to expose a portion of the liquid metal. The elastomeric fiber is integrated with an elastomeric substrate.

All combinations of the foregoing concepts and additional concepts discussed in greater detail below (provided such concepts are not mutually inconsistent) are part of the inventive subject matter disclosed herein. In particular, all combinations of claimed subject matter appearing at the end of this disclosure are part of the inventive subject matter disclosed herein. The terminology used herein that also may appear in any disclosure incorporated by reference should be accorded a meaning most consistent with the particular concepts disclosed herein.

BRIEF DESCRIPTIONS OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters refer to like features (e.g., functionally and/or structurally similar elements).

FIG. 3A illustrates a process for making a soft, stretchable, multifunctional gastric interface with one or more embedded elastomeric fibers.

DETAILED DESCRIPTION

Figure 1A:
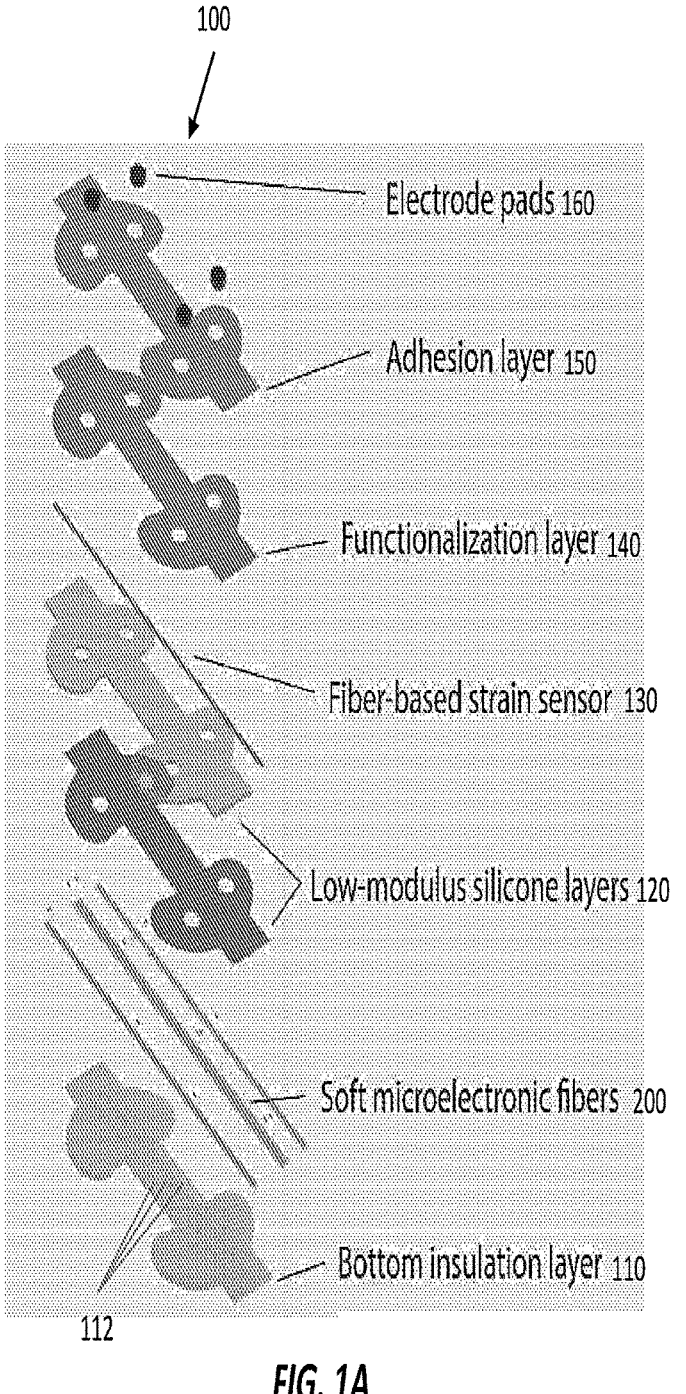
FIG. 1A shows an exploded view layout of a soft, stretchable, multifunctional bioelectronic (gastric) interface as an illustrative example.
Figure 1B:
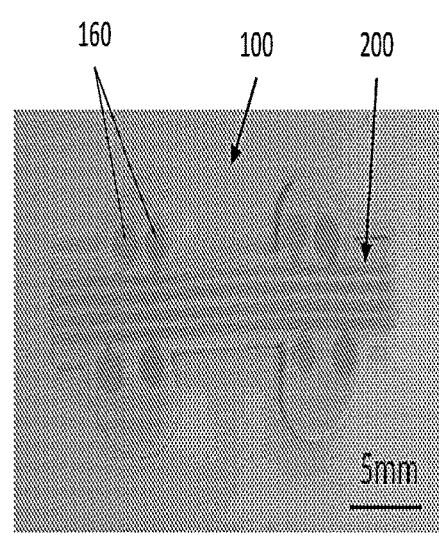
FIG. 1B is a digital image of a soft, stretchable, multifunctional gastric interface after being released from a mold.
Figure 1C:
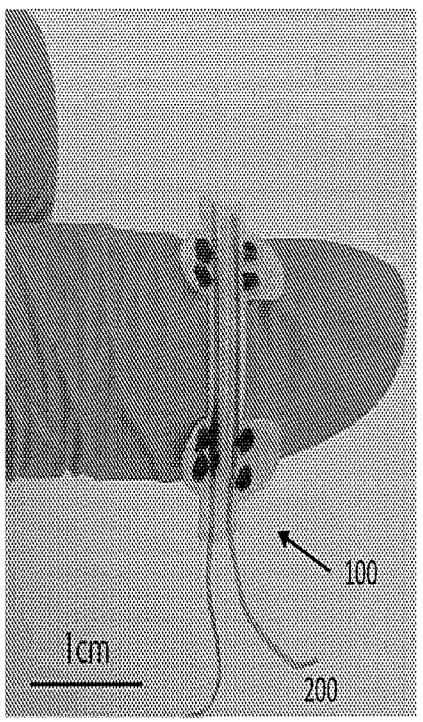
FIG. 1C is a digital image of a soft, stretchable, multifunctional gastric interface wound around a person's finger.

FIGS. 1A-1C illustrate an example of a soft, stretchable, multifunctional bioelectronic interface 100 suitable for chronic implantation on the serosal surface of the stomach. FIG. 1A shows an exploded view of the interface 100, which includes multiple layers molded together. These layers include a bottom insulation layer, or substrate 110, with channels 112 for one or more soft, microelectronic fibers 200, which may include liquid metal conductors and are described in greater detail below. Each microelectronic fiber 200 may include one or more microelectronic components, each of which is electrically connected to two liquid metal conductors (e.g., ground and +5 V channels) in the microelectronic fiber 200. Each pair of liquid metal conductors can be coupled to many microelectronic components, so long as any voltage drop is properly accounted for if the microelectronic components are coupled in parallel. Microelectronic components that are individually controlled or multiplexed can be coupled to separate interconnect traces (liquid-metal-filled conductive channels).

One or more low-modulus silicone layers 120 on the substrate 110 seal the microelectronic fibers 200 into the channels 112 and prevent liquid metal or any other substances from leaching out of the microelectronic fibers 200. Each silicone layer 120 can be 200-1000 μm thick (e.g., 200, 300, 400, 500, 750, or 1000 μm thick) and can be made of low-modulus silicone, such as Ecoflex™ silicone, or another medical-grade silicone or other suitable material. An interface 100 for a small animal may include four silicone layers 120, each of which is about 200 μm thick. An interface 100 for a human or large animal may include 8-10 silicone layers 120, each of which may be up to 1000 μm thick.

The interface 100 in FIG. 1A also includes an optional fiber-based strain sensor 130 sandwiched between the low-modulus silicone layers 120 and a functionalization layer 140, such as a polyurethane layer, which in turn is topped with a bioadhesive or adhesion layer 150. The functionalization layer 140 improves the silicone's adhesion to the adhesion layer 150, which in turn enables the implanted interface 100 to adhere or stick to the organ. The strain sensor 130 can be a piezoresistive strain sensor whose resistance changes with applied strain or piezocapacitive strain sensor with a parallel plate capacitor (e.g., defined by two liquid metal traces separated by a dielectric elastomer) whose capacitance changes with applied strain. This parallel plate capacitor can be integral with the strain sensor.

The bioadhesive 150 adheres to the surface of the organ or other tissue, keeping the interface 100 in place once it has been implanted. The functionalization layer 140 increases or improves adhesion of the silicone layer 120 to the bioadhesive 150. Silicones tend to be very inert and hence generally do not stick well to surfaces. Covalently modifying the silicone surface to install amine groups, which can form hydrogen-bonding interactions, facilitates adhesion of silicone surfaces to the bioadhesive 150. The functionalization layer 140 can be activated using $O_2$ plasma treatment, surface priming, or another suitable technique to promote adhesion of the interface 100 to the bioadhesive 150.

The interface 100 also includes (optional) soft electrode pads 160 that can be used to record electrical signals or deliver electrical stimulation. Each electrode pad 160 is in electrical contact with one or more of the liquid-metal interconnect(s) in the underlying soft microelectronic fiber(s) 200. As described in more detail below, the electrical connections between the electrode pads 160 and the liquid-metal interconnect(s) can be formed by ablating portions of the corresponding soft microelectronic fiber(s) 200 to expose the liquid metal and electrically connecting the exposed liquid metal to the soft electrodes with a low-temperature conducting epoxy. Once cured, this low-temperature conducting epoxy seals the holes, preventing the liquid metal from leaking out of the soft microelectronic fiber 200.

FIGS. 1B and 1C show photographs of a completed interface 100. The interface 100 is molded and can include optical and/or electronic components for sensing and stimulating tissue, such as strain sensors, temperature sensors, photodiodes, micro light-emitting diodes (μLEDs), or recording/stimulating electrodes. The overall size of the interface 100 depends on the application. For use in a murine stomach, the interface can be about 700 μm thick with a length of up to about 3 cm and a width of up to about 2 cm. The interface can be scaled in size to interface organs from larger species, such as pigs or humans by taking advantage of a highly scalable thermal drawing approach. For instance, an interface for a person may about 15 cm to 40 cm long, depending on the person's body mass, height, waist size, whether they have been fasting, etc.

The shape or geometry of the interface 100 can be informed by a computerized tomography (CT) scan, magnetic resonance (MR) scan, and/or other imaging modality scan. The scan(s) can be used to develop a precise master mold for the substrate (bottom insulation layer 110) and superstrate (silicone layers 120). For instance, the interface's shape may be selected or chosen to match the implant site or organ anatomy as closely as possible.

Elastomeric Fibers with Channels Filled with Liquid Metal

FIGS. 2A-2J illustrate soft, stretchable microelectronic fibers 200 for soft, stretchable, multifunctional bioelectronic interfaces (e.g., interface 100) and how they can be made. The fibers 200 can include embedded electronic and optical sensors and other components that operate even when the fibers 200 are strained thanks to strain-insensitive conductors: metal that is liquid at body temperature. These low-melting-point metals are non-toxic and fill channels that run the length of the fiber 200, connecting to components embedded or attached along the fiber's lengths and to control circuitry and power sources at one or both ends of the fiber 200.

Figure 2A:
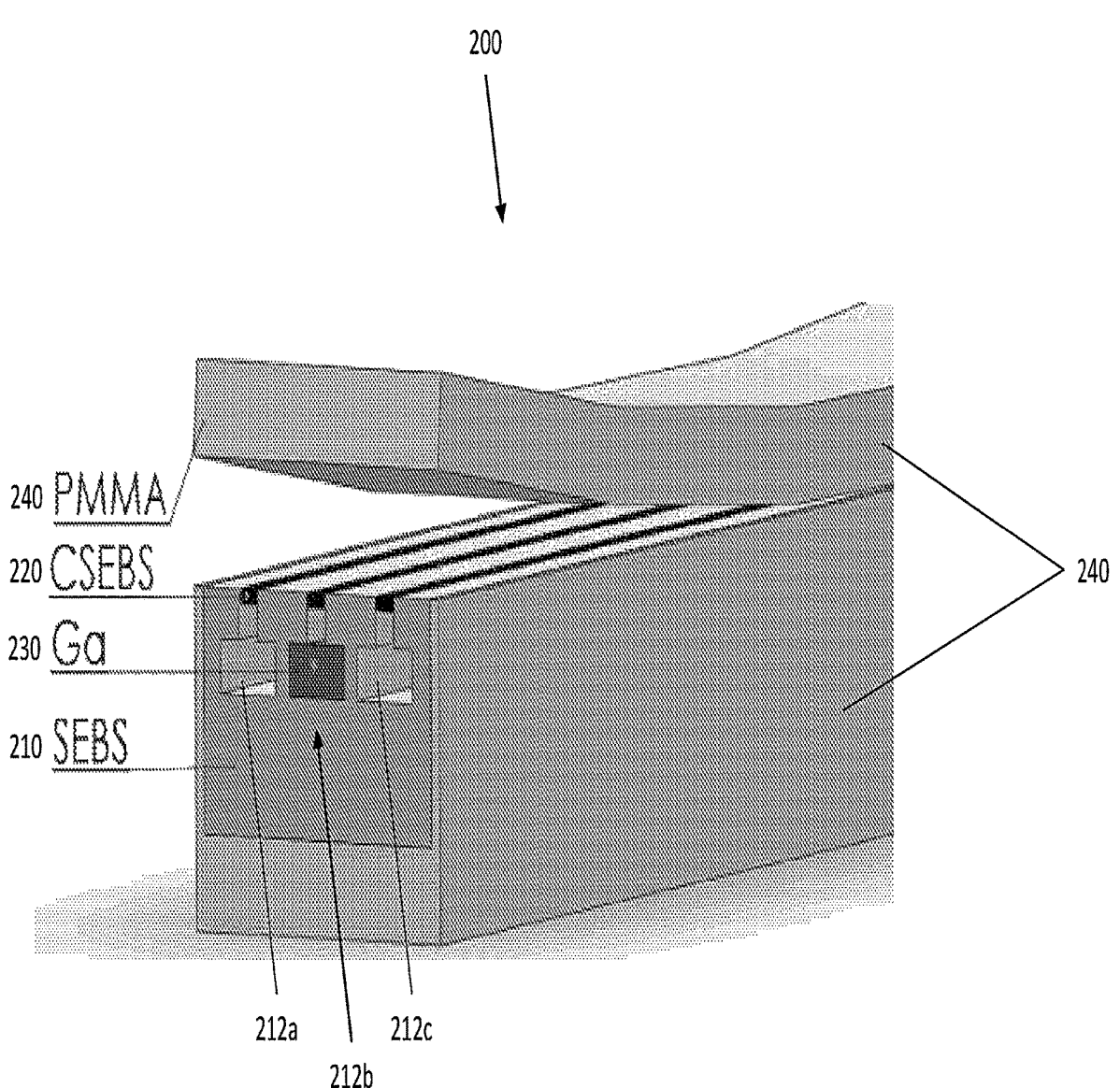
FIG. 2A is a partially exploded, perspective view of an elastomeric fiber with multiple liquid-metal-filled conductive channels that is drawn from a preform structure and can be part of a soft, stretchable, multifunctional gastric interface.
Figure 2B:
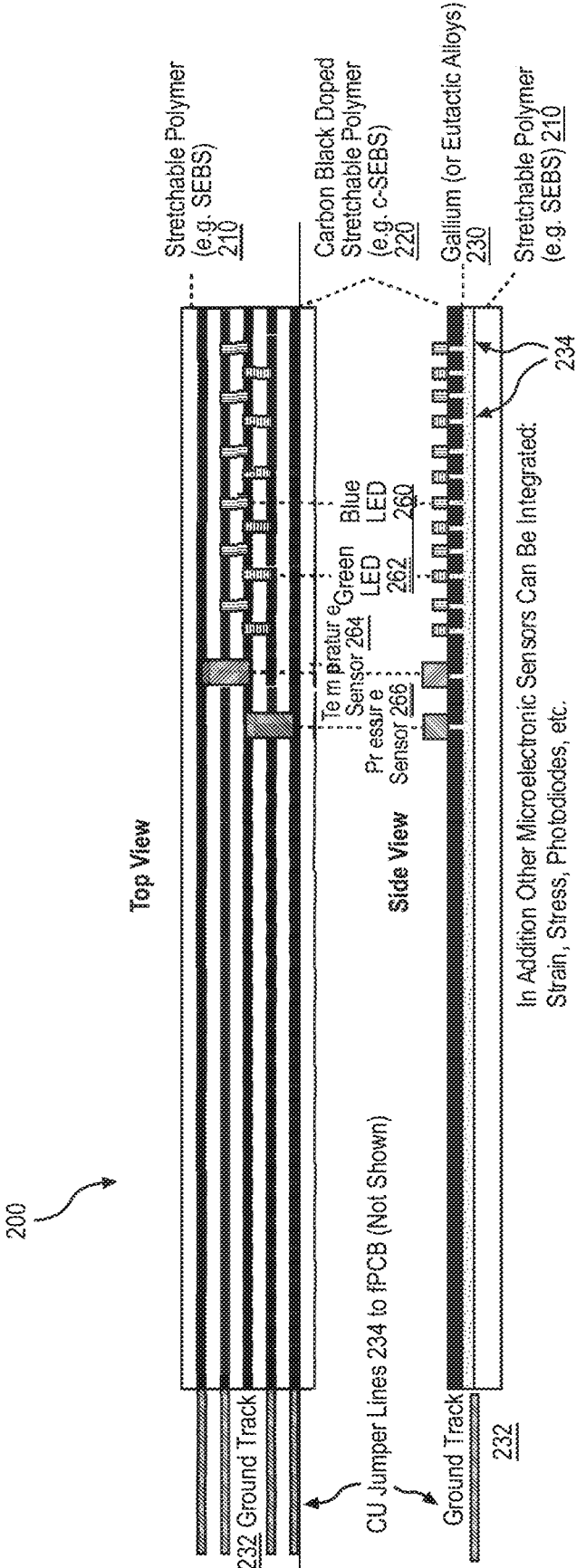
FIG. 2B shows plan and profile views of an elastomeric fiber with multiple liquid-metal-filled conductive channels electrically coupled to different microelectronic components, including a pressure sensor, temperature sensor, and green and blue LEDs.
Figures 2C, 2D, 2E:
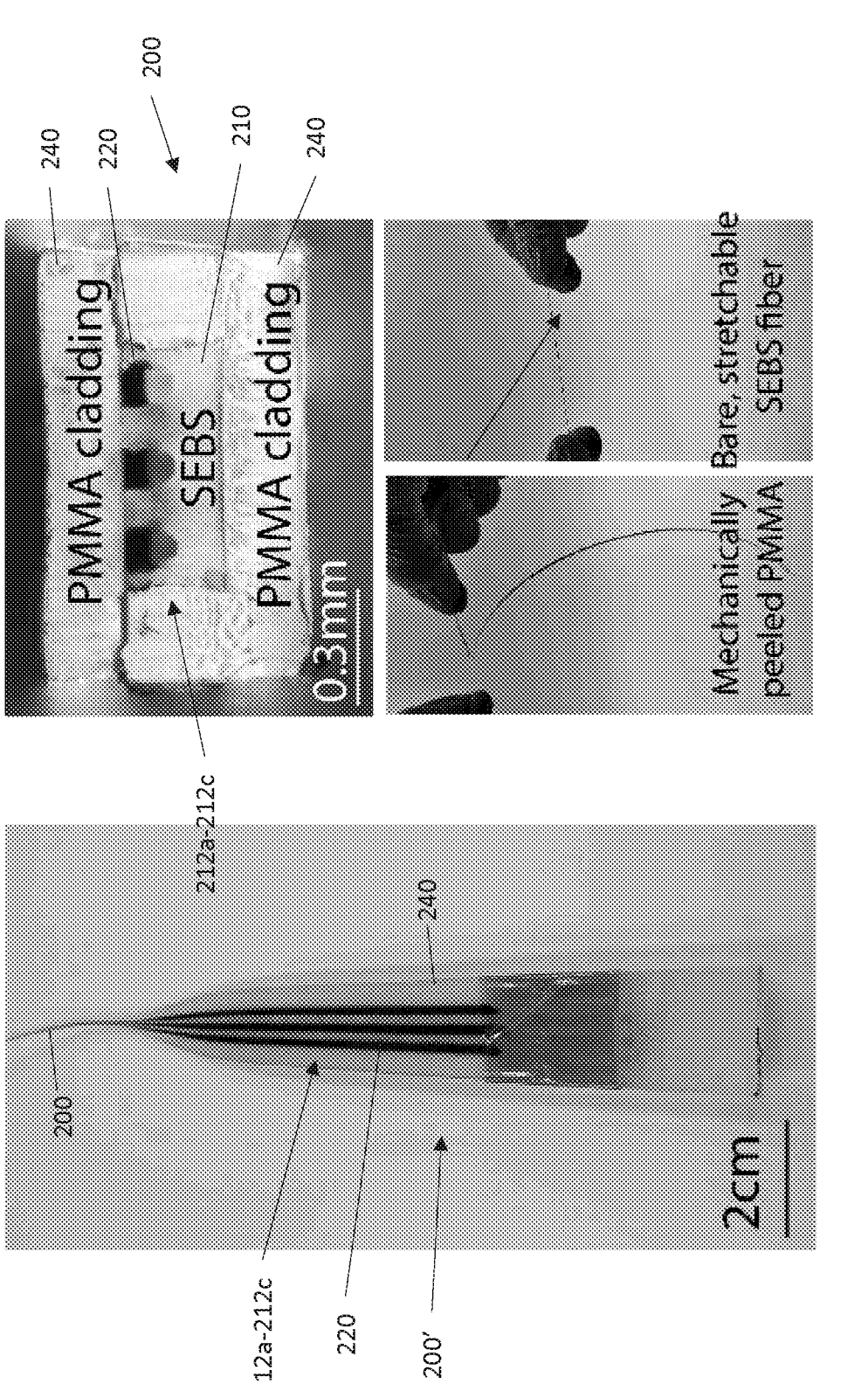
FIG. 2C is an image of a preform structure for an elastomeric fiber.
FIG. 2D is an optical micrograph of a cross-section of the multi-channel SEBS fiber and PMMA cladding drawn from the pre-form of FIG. 2C showing the conserved cross-sectional geometry of the pre-form.
FIG. 2E shows the PMMA cladding being mechanically peeled from the multi-channel SEBS fiber, exploiting weak adhesion between PMMA and SEBS (left), and the bare stretchable SEBS fiber after removal of the cladding PMMA (right).

FIGS. 2A and 2B are schematics of an elastomeric fiber 200 with and without a protective cladding 240, respectively. FIG. 2C shows a partially drawn preform 200' from which the elastomeric fiber 200 can be drawn. (In FIG. 2C, one end (top) of the preform 200' has been drawn into fiber form. Polyimide tape on the undrawn portion (bottom) to prevent the sacrificial cladding 240 from delaminating prematurely.) The preform 200' has the same basic shape and materials as the fiber 200. Like the as-drawn fiber 200, the preform 200' includes a thermoplastic elastomer, such as poly[styrene-(ethylene-co-butylene-styrene] triblock copolymer (SEBS) as the core 210, and a hard plastic, such as polymethyl methacrylate (PMMA), as a sacrificial cladding 240. The thermoplastic elastomer core 210 has holes, channels, and/or grooves to accommodate liquid metal conductors 230, electronic components, and/or optical components. In FIGS. 2A and 2C, there are three grooves or channels 212a-212c milled in one side of the thermoplastic elastomer core 210, giving it a roughly W-shaped cross section.

The channels are plugged lengthwise with highly absorbing material 220, such as carbon-doped SEBS (CSEBS) or another suitable carbon-doped thermoplastic elastomer composite, so they can be filled with liquid metal 230, such as gallium or another body- or room-temperature liquid metal, without leaking lengthwise. CSEBS 220 is a composite made by adding carbon microparticles to SEBS thermoplastic; as such, CSEBS is a thermoplastic and can be thermally drawn just like other polymers so long as the carbon percentage is within a certain range (e.g., <25 wt %). The CSEBS 220 is bonded to the bottom SEBS core 210 and to the top PMMA layers 240 of the preform 200' by thermal consolidation and continues to stay in place even after drawing. SEBS and CSEBS bond to each other very well since they essentially contain the same thermoplastic base layer. Unlike pure SEBS, which is very transparent at optical wavelengths, the CSEBS 230 also facilitates laser micromachining because its absorption coefficient is very high across the entire visible to near-infrared spectrum. The CSEBS 230 absorbs incident visible or infrared laser irradiation very efficiently and so can be ablated cleanly without thermally damage of the surrounding material (e.g., SEBS and PMMA as shown in FIG. 2C).

The preform 200' is thermally drawn to produce a microelectronic fiber 200 whose cross section has the same shape, albeit at much smaller scale, as the cross section of the preform 200'. Weak interfacial adhesion between the elastomeric (SEBS) core 210 and the PMMA sacrificial cladding 240 allows straightforward mechanical delamination (peeling) of the PMMA sacrificial cladding 240 from the elastomeric core 210 without requiring any solvent treatment. FIG. 2D shows a cross-section of the just-drawn fiber 200, and FIG. 2E shows the protective cladding 240 being peeled off the fiber (left) to leave the bare fiber (right).

The elastomeric (SEBS) core 230 can be designed in various shapes, such as ribbons, and can include multiple microscale (e.g., 50-100 μm wide) hollow channels that have a well-defined pitch size. These grooves or channels extend all the way along the length of the elastomeric core. If desired, two or more elastomeric cores can be placed back-to-back or side-to-side to yield an elastomeric fiber that is larger and includes more grooves or channels. The elastomeric cores can also be placed face-to-face, with aligned cores, to yield an elastomeric fiber with larger grooves.

One or more of the channels 212a-212c in the as-drawn fiber 200 are filled with a room-temperature liquid metal or soft metal conductor 230, such as Gallium (super cooled state), eutectic Gallium-Indium, or Gallium-Indium-Tin (Galinstan) alloy. Gallium is non-toxic and has a melting point of about 30° C. Eutectic Gallium-Indium and Galinstan have melting points of about 15.7° C. and −19° C., respectively. This means that Gallium, eutectic Gallium-Indium, and Galinstan are liquid and therefore insensitive to strain at a typical body temperature of about 37° C.

The holes or channels in the elastomeric fiber 200 can be filled with liquid metal 230 during the thermal drawing process or after thermal drawing. Before drawing, the liquid metal 230 can be poured into a channel in the preform 200'. This channel is sealed at its bottom to prevent the liquid metal 230 from leaking out. The preform 200' is then drawn to form the elastomeric fiber 200. Alternatively, the liquid metal 230 can be drawn or sucked into a groove or channel after the elastomeric fiber 200 has been drawn, e.g., through capillary action. The fiber 200 is cut into segments before the liquid metal channels are coupled to the microelectronic components as described below, and the channels are capped or sealed, e.g., with medical-grade silicone, to prevent the liquid metal 230 from leaking out.

Any hollow channel in the fiber that is to be accessed from a fiber face is marked with a material 220 with a high optical absorption coefficient, such as SEBS-carbon nanocomposite 220 (3% by weight), on the access site. This includes hollow channels 212a-212c filled with liquid metal. Vertical interconnect accesses (via) ports are patterned onto the fiber 200 using a laser micromachining process (before or after metal filling) that exposes the liquid-metal interconnects. A high-power pulsed laser beam illuminates the highly absorbing material 220, which absorbs the incident laser light. This ablates the marked portion(s) of the fiber 200, creating windows, holes, or vias 234 through the fiber 200 to the hollow channel 212 without damaging the material (e.g., liquid metal 230) in the hollow channel 212. The liquid metal 230 may flow through these holes to the holes 234 via capillary action.

If the hollow channel 212 is filled with liquid metal 230, the window exposes a liquid metal pad that can be electrically connected to an electronic component, such as a microelectronic sensor or actuator. Example microelectronic sensor and actuator components include different color microscale light emitting diodes (μLEDs) 260 and 262, photodiodes, thermal sensors 264, and pressure transducers 266, all of which can be mounted onto the exposed liquid metal pads. In FIG. 2B, the μLEDs 260 and 262, thermal sensor 264, and pressure transducer 266 are all electrically coupled to a common ground liquid-metal interconnect 232 and to separate control liquid-metal interconnects (indicated by liquid metal 230). Once the microelectronic components have been mounted, they are electrically insulated using a medical-grade silicone. The silicone also keeps the components in place with respect to the fiber 200 and prevents the liquid metal 230 from leaking out of the fiber 200. In other words, the silicone forms a seal around the hole in the CSEBS 220 and the microelectronic component(s).

The liquid-metal-filled or soft-metal-filled channels 212 in the polymer fiber can also be connected to a flexible printed circuit board (fPCB) using copper microwires as jumper lines 232 that stick into the open ends of the channels. In a small animal, the fPCB can be fully implanted in the subcutaneous space on the animal's back or fixed on the animal's skull surface. For humans and larger animals, the fPCB can be either integrated into the mold or wired and then placed in a natural anatomic cavity (e.g., like a pacemaker cavity). For a small animal, the fPCB may host circuitry and corresponding electrical components for wireless and/or wired operation. This circuitry can control the microelectronic sensors and/or actuators disposed along the fiber's length. For wired operation, the fPCB mainly serves as an interface between a controlling instrument and the bioelectronic interface's microelectronic components (e.g., by housing amplifier circuits, voltage dividers, Bluetooth radio, microcontrollers, etc.). For wireless operation, the fPCB can hold pins that can be connected to a battery to power the electronics (e.g., in a small animal) or can accommodate an integrated battery (e.g., in a large animal or human). The fPCB can also support transmission and receiving coils to wirelessly send and receive stimulation patterns and recordings in real-time.

Figure 2G:
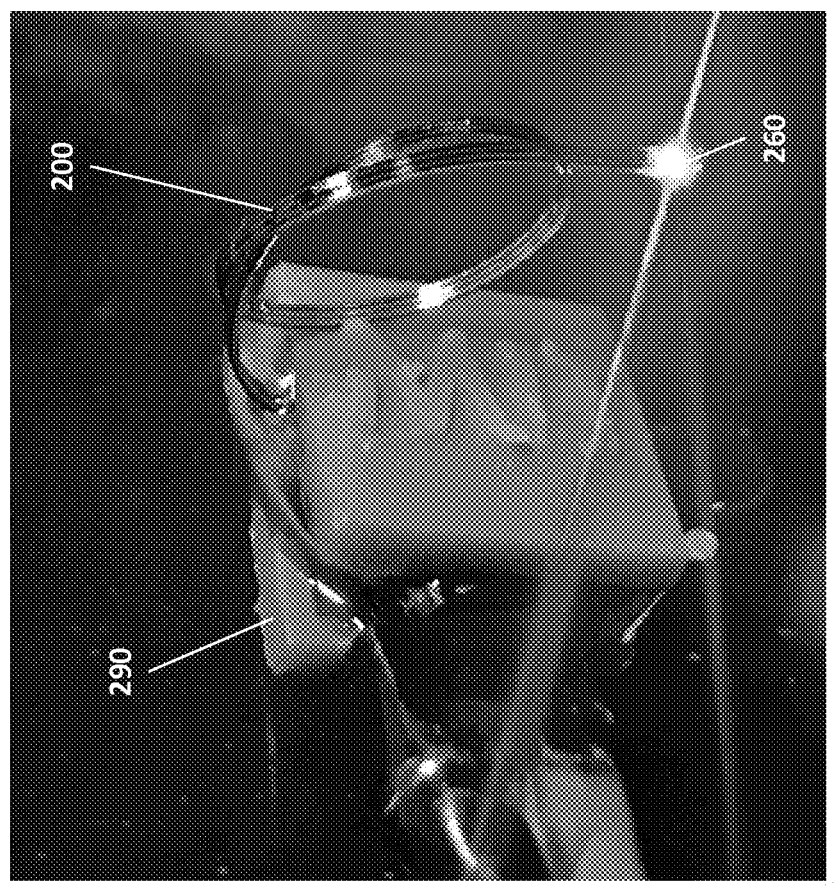
FIG. 2G shows a bent/strained soft, microelectronic fiber with liquid-metal-filled channels connected to an embedded micro-light emitting diode (μLED).
Figure 2F:
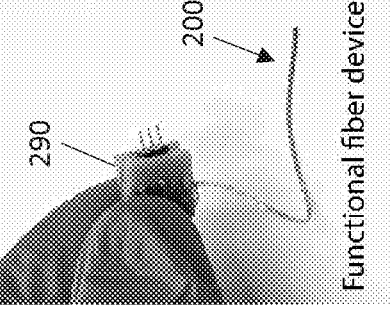
FIG. 2F is a digital image of a fully functional soft, stretchable, multifunctional gastric interface made from the soft, microelectronic fiber in FIG. 2E.

FIGS. 2F and 2G illustrate a fabricated elastomeric fiber 200 complete with embedded microelectronics, including an embedded μLED 260, and liquid-metal-filled conductive channels 230 coupled to a packaged fPCB 290 at one end of the fiber 200. The fiber 200 is soft and flexible, as shown in FIGS. 2F and 2G, which show the fiber bent or wound tightly. Even though the fiber 200 is bent or strained, the liquid-metal-filled conductive channels 230 remain intact and conduct electrical power and carry signals to the embedded μLED 260, shown emitting light in FIG. 2G.

Figure 2H:
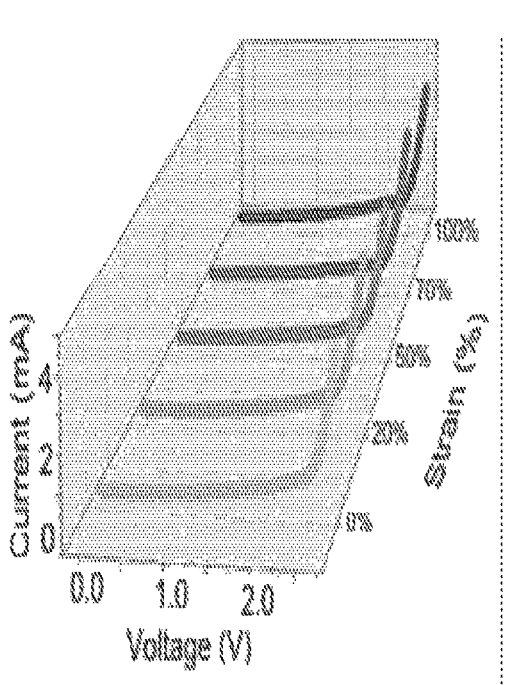
FIG. 2H is a plot of current-voltage profiles of the μLED embedded in the fiber of FIG. 2G under different applied strains.

FIG. 2H is a plot of current-voltage profiles of the μLED fiber in FIG. 2G under different applied strains and shows that the current-voltage profiles remain invariant when the fiber is subject to 100% strain, which is much larger than strains the device may experience upon implantation (typically <20%). In contrast, inflexible fibers tend to break when stretched, even at only about 5% elongation.

Figure 2I:
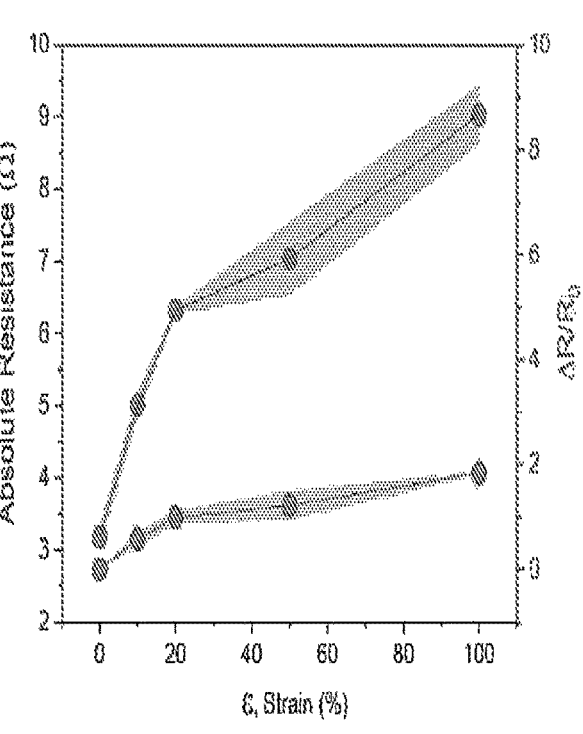
FIG. 2I is a plot of the resistance of the Gallium-filled conductive channels versus strain in the soft, microelectronic fibers shown in FIGS. 2F and 2G.

FIG. 2I is a plot of the resistance of the Gallium-filled conductive channels versus strain in the soft, microelectronic fiber 200 shown in FIGS. 2F and 2G. The left axis shows absolute resistance in ohms and the right axis shows the fractional change in resistance of the Gallium-filled conductive channels. An increase in strain from 0% to 100% causes the absolute resistance to roughly triple, from about 3Ω to about 9Ω, and the fractional change in resistance to increase from 0 to about 2.

Figure 2J:
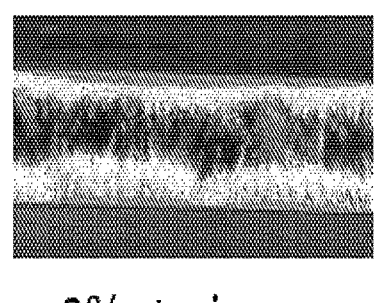
FIG. 2J shows micrographs of intact liquid gallium-filled interconnects in the fiber without any voids or discontinuities when stretched up to 100% strain.
Figure 2J:
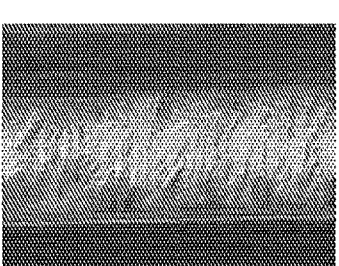
Figure 2J:
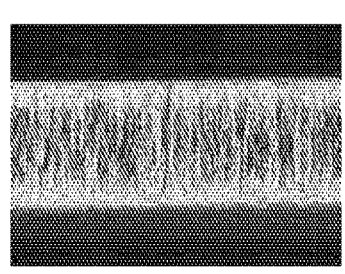
Figure 2J:
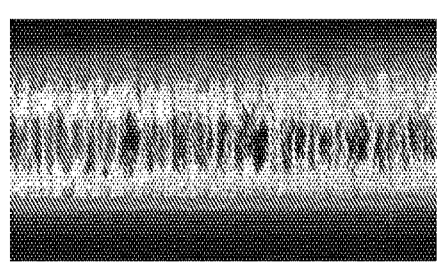
Figure 2J:
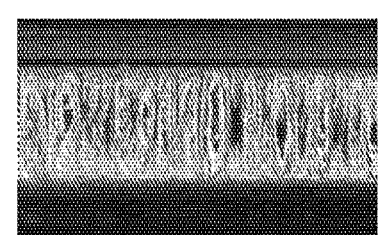

FIG. 2J shows micrographs of intact gallium-filled interconnects in elastomeric fiber without any voids or discontinuities when stretched up to 100% strain. In particular, the micrographs show gallium-filled interconnects in the fiber stretched a 0%, 20%, 50%, 75%, and 100% strain.

One or more elastomeric fibers with liquid-metal-filled channels and embedded microelectronic components can be integrated with an elastomeric substrate (e.g., the bottom insulation layer 110 in FIG. 1A) to produce a bioelectronic interface like the ones shown in FIGS. 1A-1C. For a bioelectronic interface intended to adhere to the surface of an organ (e.g., the surface of the stomach or intestines), one or more elastomeric fibers (e.g., fibers 200) are molded or fitted into grooves or hollows in a patterned elastomeric substrate made of low-modulus silicone (about 40-60 kPa), where the substrate itself is produced by molding from 3D printed positive-master mold. The positive master-mold for the patterned elastomeric substrate can be designed such that it matches the anatomical features of the desired organ using commercial computer-aided design (CAD) software. A low-modulus silicone superstrate (e.g., including the silicone layers 120 in FIG. 1A) can be prepared in a similar way (e.g., molded) and bonded to the fiber-carrying substrate with a thin interlayer of silicone adhesive. The superstrate may have openings at desired locations that allow fabrication of soft electrodes (e.g., the electrode pads 160 in FIG. 1A) for electrical recording or stimulation.

Fabrication and Performance of a Bioelectronic Interface with Elastomeric Fibers FIG. 3A illustrates a method 300 for making a soft, stretchable bioelectronic interface like the one shown in FIGS. 1A-1C with an elastomeric fiber like the one shown in FIG. 2A. The fiber is made in a multi-step process that starts with making a preform (310) with an elastomeric core and sacrificial layer like the one shown in FIG. 2C. The preform can be made by forming one or more groves (312) in an elastomeric core, then plugging the length of the groove with an optically absorbing material (314) to form one or more hollow channels that runs the length of the elastomeric core. The preform is drawn (320) to form the elastomeric fiber, with liquid metal disposed in the hollow channel(s) (330) either before or after drawing as described above. Removing the sacrificial out layer leaves the bare fiber (340). Microelectronic components are integrated with the fiber by ablating holes (350) in the optically absorbing material to expose the liquid metal, then electrically connecting (360) the microelectronic components to the liquid metal before sealing (370) around the holes with silicone or another suitable material to prevent the liquid metal from leaking out of the hollow channel(s). The elastomeric fiber is disposed in a groove, channel, or hollow in an elastomeric substrate (380), with silicone layers placed on the elastomeric substrate (390) to secure the elastomeric fiber in place.

Figure 3B:
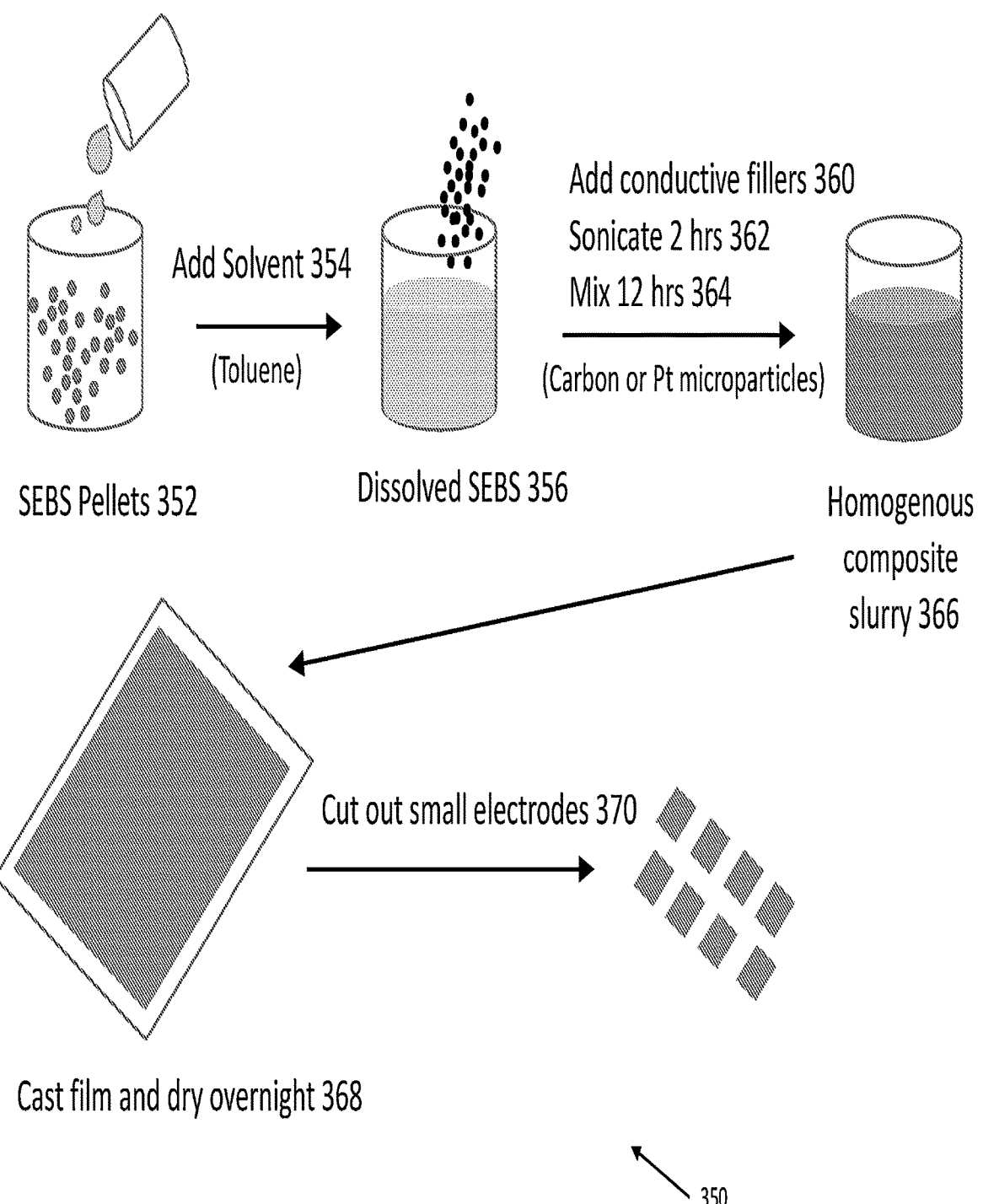
FIG. 3B illustrates a process for making soft electrodes suitable for integration with a soft, stretchable, multifunctional gastric interface with one or more embedded elastomeric fibers.

FIG. 3B illustrates a process 350 for making soft electrodes (e.g., soft electrodes 160 in FIG. 1A) for use in a soft, stretchable bioelectronic interface. The process 350 begins with dissolving polymer (e.g., SEBS) pellets 352 in a solvent, such as toluene (354), to produce dissolved SEBS 356. Next conductive fillers, such as carbon or platinum (Pt) microparticles, are added to the dissolved SEBS (360). The dissolved SEBS/conductive fillers mixture is sonicated (362), e.g., for two hours, and mixed (364), e.g., for twelve hours, to produce a homogeneous composite slurry 366 of conductive material. This slurry is spread in a layer on a piece of film or another suitable substrate (368) and allowed to dry before being cut into small, soft electrodes (370) of suitable shapes and dimensions. These soft electrodes can be integrated into an interface as described above with respect to FIG. 1A.

Figure 4A:
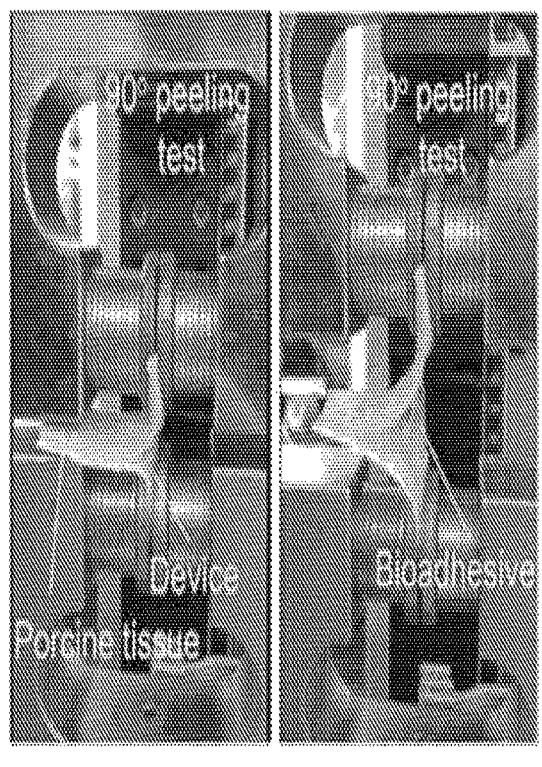
FIG. 4A shows digital images of a fully functional soft, stretchable, multifunctional gastric interface under test during different stages of a 90° peeling test with a polyacrylamide-based bioadhesive.
Figure 4B:
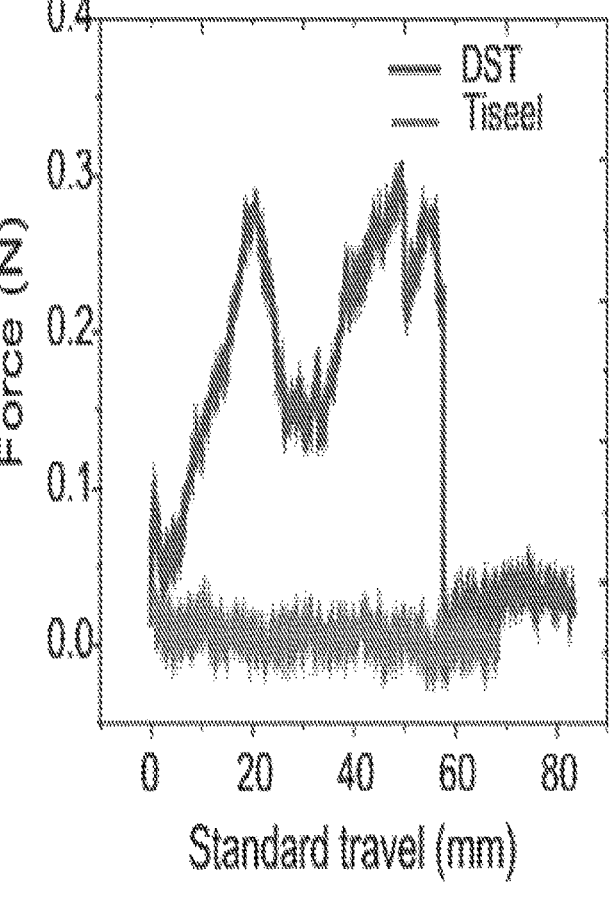
FIG. 4B is a plot of the force of adhesion versus standard travel for a double-sided-tape (DST) bioadhesive (upper trace) and a Tisseel bioadhesive (lower trace).

FIGS. 4A and 4B illustrate performance of a bioelectronic interface like the one shown in FIGS. 1A-1C. FIG. 4A shows digital images of a fully functional soft, stretchable, multi-functional gastric interface under test during different stages of a 90° peeling test with a polyacrylamide-based bioadhesive. In the peeling test, the interface is bonded to porcine stomach tissue with the bioadhesive. FIG. 4B is a plot of the force of adhesion versus standard travel for a double-sided-tape (DST) (upper trace) and a Tisseel fibrin sealant (lower trace), which acts as a bioadhesive. The traces in FIG. 4B quantify the force of adhesion with and without bioadhesive. Use of bioadhesive to robustly bond a device to an organ surface in a minimally invasive manner obviates the need to add (more invasive) sutures for the same purpose. This is particularly true for fragile organs or hard-to-reach sites where application of a suture can be traumatic or infeasible.

Organ Interfacing and Neuromodulation

A low-modulus and stretchable multifunctional interface can be laminated onto a curved organ such as the stomach and fixed in place using a bioadhesive in a minimally invasive fashion. In a human, for example, an interface be implanted by: (a) endoscopically laminating the interface on the mucosa of stomach/small and large intestines; (b) endo-scopically inserting the interface into the stomach/small and large intestine wall (placing the device between mucosal and serosal side; or (c) laparoscopically inserting the interface and laminating it on outer organ surfaces, e.g., an outer surface of the stomach or bladder.

Once implanted, an interface can perform neuromodula-tion by electrically and/or optically stimulating the organ innervating vagal afferents/efferents and recording physi-ological parameters (e.g., local tissue temperature, strain) with temperature and strain sensors. It can perform closed loop-modulation using the organ conditions as the input, the electrodes and/or μLEDs as output sources, and the sensor signals as error or feedback signals. The implanted device can also be controlled wirelessly using miniature flexible circuits with wireless transducers.

Example: Closed-Loop Optical Gastric Pacing in Gastroparesis

Conventional bioelectronic therapy relies on electrical stimulation of nerve bundles and lacks organ specificity. Direct interfacing of electrodes onto delicate nerves may also lead to injury and inflammation. In contrast, soft, stretchable, multifunctional bioelectronic interfaces with embedded μLEDs can optically stimulate targeted nerves that are genetically modified to express light-sensitive opsins. These interfaces can also (continuously) record biophysical signals using high-precision sensors.

An example use case for such as interface is monitoring and treating disorders of the gastrointestinal tract, such as gastroparesis, which is commonly encountered in patients diagnosed with Parkinson's disease and chronic diabetes mellitus. Gastroparesis affects spontaneous gastric muscle movement and can lead to abnormal stomach emptying episodes.

In a gastroparesis patient, following an abdominal CT or MRI scan, a soft, stretchable bioelectronic interface hosting multiple independently addressable μLEDs, a strain sensor, thermal sensors, and multiple soft electrodes for recording gastric myoelectrical activity is custom fabricated to match the anatomy of the patient's stomach. Surgical implantation allows lamination of one of the device's outer layers onto the whole organ. Once implanted, the device can continuously track the stomach distension following a meal through the following physiological parameters: (1) changes in strain levels corresponding to changes in stomach volume; (2) change(s) in local temperature due to increased blood flow to the stomach; and (3) changes in gastric neuromuscular activity. Strain and temperature sensors embedded in the interface detect the strain and temperature changes. Soft electrodes on the device can record electrical activity of gastrointestinal muscle (electrogastrography). The detection of these signals can in turn trigger patterns of optical (or electrical) stimulation with the μLEDs (or stimulating elec-trodes) embedded in the interface. The stimulation helps to recapitulate normal physiological peristalsis activity of the gastric muscles, which can be stopped as the stomach volume returns to its baseline level as inferred from the readings of the strain and thermal sensors.

CONCLUSION

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exem-plary and that the actual parameters, dimensions, materials, and/or configurations will depend upon the specific appli-cation or applications for which the inventive teachings is/are used. Those skilled in the art will recognize or be able to ascertain, using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be prac-ticed otherwise than as specifically described and claimed. Inventive embodiments of the present disclosure are directed to each individual feature, system, article, material, kit, and/or method described herein. In addition, any combina-tion of two or more such features, systems, articles, mate-rials, kits, and/or methods, if such features, systems, articles, materials, kits, and/or methods are not mutually inconsis-tent, is included within the inventive scope of the present disclosure.

Also, various inventive concepts may be embodied as one or more methods, of which an example has been provided. The acts performed as part of the method may be ordered in any suitable way. Accordingly, embodiments may be con-structed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of" "only one of" or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. An implantable apparatus for interfacing with an organ, the implantable apparatus comprising:
   an elastomeric substrate having a channel formed in a surface thereof;
   an elastomeric fiber disposed in the channel, the elastomeric fiber defining a hollow channel;
   liquid metal disposed in the hollow channel;
   a plurality of layers disposed on the surface of the elastomeric substrate over the channel; and
   a microelectronic component, disposed on an outer layer of the plurality of layers and in electrical communication with the liquid metal, to stimulate and/or sense the organ in response to an electrical signal and/or electrical power conducted by the liquid metal.

2. The implantable apparatus of claim 1, wherein the liquid metal comprises at least one of Gallium, eutectic Gallium-Indium, or Gallium-Indium-Tin alloy.

3. The implantable apparatus of claim 1, wherein the liquid metal is non-toxic and has a melting point of less than 37° C.

4. The implantable apparatus of claim 1, further comprising a micro light-emitting diode to optically stimulate the organ.

5. The implantable apparatus of claim 1, further comprising a temperature sensor to sense a temperature of the organ.

6. The implantable apparatus of claim 1, wherein at least one layer of the plurality of layers comprises:
   at least one silicone layer disposed on the elastomeric substrate over the channel.

7. The implantable apparatus of claim 6, wherein at least one layer of the plurality of layers comprises:
   an adhesive layer, disposed on the at least one silicone layer, to adhere the implantable apparatus to a surface of the organ.

8. The implantable apparatus of claim 7, further comprising:
   a strain sensor, disposed between the elastomeric substrate and the adhesive layer, to sense strain experienced by the organ.

9. The implantable apparatus of claim 7, wherein at least one layer of the plurality of layers comprises:
   a functionalization layer, disposed between on the at least one silicone layer and the adhesive layer, to increase adhesion of on the at least one silicone layer to the adhesive layer.

10. The implantable apparatus of claim 6, wherein the at least one silicone layer comprises at least four silicone layers, each having a thickness of at least 200 μm.

11. The implantable apparatus of claim 6, wherein the at least one silicone layer comprises at least eight silicone layers, each having a thickness of about 1000 μm.

12. The implantable apparatus of claim 1, further comprising:
   an optically absorbing material plugging a length of the hollow channel.

13. A method of making an implantable apparatus for interfacing with an organ, the method comprising:
   forming a preform comprising an elastomeric core and a sacrificial outer layer, the elastomeric core defining a hollow channel;
   drawing the preform to form an elastomeric fiber having the hollow channel oriented along a length of the elastomeric fiber;

removing the sacrificial outer layer from the elastomeric fiber;

disposing liquid metal in the hollow channel;

forming an electrical connection between the liquid metal and a microelectronic component, the microelectronic component in electrical communication with the liquid metal and adapted to stimulate and/or sense the organ in response to an electrical signal and/or electrical power conducted by the liquid metal; and integrating the elastomeric fiber with an elastomeric substrate, wherein integrating the elastomeric fiber with the elastomeric substrate comprises:

disposing the elastomeric fiber in a channel formed on a surface of the elastomeric substrate; and disposing a plurality of layers over the elastomeric substrate and the channel.

14. The method of claim 13, wherein the liquid metal is non-toxic and has a melting point of less than 37° C.

15. The method of claim 13, wherein forming the preform comprises:

defining a groove along a length of the elastomeric core; and plugging the groove lengthwise with an optically absorbing material to form the hollow channel.

16. The method of claim 15, wherein forming the electrical connection comprises:

ablating a hole in the optically absorbing material to expose a portion of the liquid metal;

disposing the microelectronic component in electrical communication with the liquid metal through the hole; and

forming a seal about the hole to prevent the liquid metal from leaking out of the hollow channel.

17. The method of claim 15, wherein the elastomeric core comprises a poly[styrene-(ethylene-co-butylene-styrene] tri-block copolymer (SEBS), the optically absorbing material comprises carbon-doped SEBS, and the sacrificial outer layer comprises polymethyl methacrylate (PMMA).

18. The method of claim 13, wherein disposing the liquid metal in the hollow channel comprises disposing the liquid metal in the hollow channel before drawing the preform.

19. The method of claim 13, wherein disposing the liquid metal in the hollow channel comprises disposing the liquid metal in the hollow channel after drawing the preform.

20. A multi-layer implantable apparatus for interfacing with an organ, the multi-layer implantable apparatus comprising:

an elastomeric substrate with a groove extending along an outer surface of the elastomeric substrate;

a microelectronic fiber disposed in the groove, the microelectronic fiber comprising a liquid metal conductor;

a plurality of layers disposed over the outer surface of the elastomeric substrate and sealing the microelectronic fiber in the groove; and at least one of a sensor or an actuator disposed on an outer surface of the multi-layer implantable apparatus and electrically coupled to the microelectronic fiber, to stimulate and/or sense the organ in response to an electrical signal and/or electrical power conducted by the liquid metal conductor.

* * * * *